United States Patent [19]

Siuta et al.

[11] 4,391,824

[45] Jul. 5, 1983

[54] UREYLENEBIS (HYDROXY NAPHTHALENESULFONIC ACIDS)

[75] Inventors: Gerald J. Siuta; Seymour Bernstein, both of New City, N.Y.

[73] Assignee: American Cyanamid Company, Stamford, Conn.

[21] Appl. No.: 286,736

[22] Filed: Jul. 27, 1981

[51] Int. Cl.³ .......................................... A61K 31/185
[52] U.S. Cl. .................................................. 424/315
[58] Field of Search .......................... 260/506; 424/315

[56] References Cited

U.S. PATENT DOCUMENTS 4,046,805 9/1977 Bernstein et al. .................... 260/560
4,127,602 11/1978 Bernstein et al. .................... 260/560
4,129,591 12/1978 Bernstein et al. .................... 260/560

Primary Examiner—Stanley J. Friedman
Attorney, Agent, or Firm—Anne M. Rosenblum

[57] ABSTRACT

Methods of use and compositions of matter of certain ureides of substituted naphthalenesulfonic acids and salts thereof, useful as inhibitors of connective tissue destruction.

15 Claims, No Drawings

UREYLENEBIS (HYDROXY NAPHTHALENESULFONIC ACIDS)

BACKGROUND OF THE INVENTION

1. Field of Invention

The present invention resides in methods of use and compositions of matter of certain ureylenebis-[(substituted or unsubstituted-phenylenecarbonylimino)bis-(substituted-naphthalenesulfonic acids)] and salts thereof, being useful as inhibitors of connective tissue destruction.

2. Description of the Prior Art

Abnormal destruction of connective tissue by collagenase and/or neutral proteases causes tissue damage and/or tissue dysfunction. In these conditions an inhibitor of connective tissue destruction acting directly or indirectly would be useful in preventing, retarding, or reversing tissue damage and/or collagen diseases.

The term connective tissue refers to a matrix of at least three protein molecules: collagen, proteoglycan and elastin. These molecules play an important role in the structural integrity of normal tissues. Collagen, the most abundant protein in the body occupies a central position in the connective tissue matrix ["Biochemistry of Collagen," Ed. G. N. Ramachandran and A. H. Reddi, Academic Press, N.Y. (1976); P. Bornstein, Annu. Rev. Biochem. 43: 567 (1974); J. Fessler and L. Fessler, Annu. Rev. Biochem. 47: 129 (1978)].

Collagen is, for example, the main structural component of the oral tissue (periodontal ligament, alveolar bone, gingiva, and cementum) [Fullmer, et al., J. Dent. Res. 48: 646 (1969)]. Collagen amounts to 40% of cartilage protein, 90% of bone protein, and over 90% of dry dermis. Articular cartilage is the resilient tissue that covers the articulating extremities in synovial joints. It consists of collagen fibres that are intimately meshed in a hydrated gel of proteoglycan.

Proteoglycan, as it exists in cartilage, is a molecule in which sulfated polysaccharide chains are covalently linked to a protein backbone ["Dynamics of Connective Tissue Macromolecules," Ed. P. M. Burleigh and A. R. Poole, North Holland, Amsterdam (1975)].

Elastin is a major connective tissue component of pulmonary structure ["Elastin and Elastic Tissue," Ed. L. B. Sandberg, W. R. Gray, and C. Franzblau, Plenum Press, N.Y. (1977)]. The breakdown of elastin of pulmonary connective tissue is considered the primary event in pulmonary emphysema [A. Janoff in "Proteases and Biological Control," Cold Spring Harbor Conf. Cell Proliferation 2: 603 (1975)].

Degradation of fibrous collagen is initiated by a combination of neutral proteases and tissue collagenase as an integral part of a complex immunopathological process which results in the loss of collagen from normal tissue. Under normal conditions cellular mechanisms maintain a careful balance between the rates of collagen synthesis and degradation. However, in certain pathological conditions, the ensuing elevated levels of neutral proteases and collagenase can result in rapid collagen degradation and tissue dysfunction. For example, in periodontal disease, the generated elevated levels of neutral proteases and collagenase in the gingival crevicular fluid rapidly degrade the fibrous collagen supporting the teeth. Periodontal pockets result ultimately from collagen degradation, and as these pockets deepen, support of tooth is lost and alveolar bone is resorbed [K. Ohlsson, I. Ohlsson, and G. I. Basthall, Acta Odontol. Scand. 32: 51 (1974) L. M. Golub, S. Kenneth, H. McEwan, J. B. Curran, and N. S. Ramamurthy, J. Dent. Res. 55: 177 (1976); L. M. Golub, J. E. Stakin and D. L. Singer, J. Dent. Res. 53: 1501 (1974); L. M. Wahl, S. M. Wahl, S. E. Mergenhagen, and G. R. Martin, Proc. Natl. Acad. Sci. U.S.A. 71: 3598 (1974); Science, 187: 261 (1975)].

In arthritic conditions such as in rheumatoid arthritis, septic arthritis, and osteoarthritis elevated degradation of collagen and proteoglycan initiates rapid destruction of articular tissue [J. M. Evanson, J. J. Jefferey, and S. M. Krane, Science 158: 499 (1967); E. D. Harris, D. R. Dibona and S. M. Krane, J. Clin. Invest. 48: 2104 (1969); E. D. Harris, Rheumatoid Arthritis, Medcom. Press, N.Y. (1974); Z. Werb, C. L. Mainardi, C. A. Vater and E. D. Harris, N. Engl. J. Med. 296: 1017 (1977); J. M. Dayer, R. G. Russell and S. M. Krane, Science 195: 181 (1977); E. D. Harris, C. A. Vater, C. L. Mainardi and Z. Werb, Agents Actions 8: 35 (1978); D. E. Woolley, E. D. Harris, C. L. Mainardi and C. E. Brinkerhoff, Science 200: 773 (1978): E. D. Harris, C. S. Faulkner, F. E. Brown, Clin. Orthop. 110: 303 (1975); M. G. Ehrlich, H. J. Mankin, H. Jones, R. Wright and C. Crisper, J. Bone Jt. Surg. 57A: 565 (1975); S. Gordon, W. Newman and B. Bloom, Agents Actions 8: 19 (1978); "Mechanisms of Tissue Injury With Reference to Rheumatoid Arthritis," Ed. R. J. Perper, Ann. N.Y. Acad. Sci. 256: 1-450 (1975)].

Increased collagen degradation in bone can result in abnormal bone destruction as in osteoporosis [C. G. Griffith, G. Nichols, J. D. Asher and B. Flannagan, J. Am. Med. Assoc. 193: 91 (1965); B. Gardner, H. Gray and G. Hedyati, Curr. Top. Surg. Res. 2: 175 (1970); B. Gardner, S. Wallach, H. Gray and R. K. Baker, Surg. Forum 22: 435 (1971)]. Collagenase activity has also resulted in tissue damage in cholesteatoma [M. Abramson, R. W. Schilling, C. C. Huang and R. G. Salome, Ann. Otol. Rhinol. Laryngol. 81: 158 (1975): M. Abramson and C. C. Huang, Laryngoscope 77: 1 (1976)]. In corneal ulcerations that progress to loss of corneal integrity and function, collagenase has been implicated as a direct factor in corneal destruction [S. I. Brown, C. W. Hook and N. P. Tragakis, Invest. Ophthalmol. 11: 149 (1972); M. B. Berman, C. H. Dohlman, P. F. Davison, and M. Ghadinger, Exp. Eye Res. 11: 225 (1971)]. Elevated levels of collagenase have also been observed in patients with epidermolysis bullosa, and a group of related genetic diseases of the skin [E. A. Bauer, T. G. Dahl, and A. Z. Eisen, J. Invest. Dermatol. 68: 119 (1977)].

Increased breakdown of elastin of the lung tissue by neutral proteases (elastase) may contribute to the lesions in pulmonary emphysema [I. Mandel, T. V. Darmle, J. A. Frierer, S. Keller and G. M. Turino, "Elastin and Elastic Tissue," Ed. L. B. Sandberg, W. R. Gray and C. Fransblau, Plenum Press, N.Y., p. 221 (1977)].

A variety of substances, both naturally occurring and synthetically prepared, have been found to be inhibitors of connective tissue destruction, e.g., inhibitors of collagen degradation, that is, as collagenase inhibitors. Such substances include, for example, ethylenediaminetetraacetate, 1,10-phenanthroline, cysteine, dithiothretol and sodium auriothiomalate [D. E. Woolley, R. W. Glanville, D. R. Roberts and J. M. Evanson, Biochem. J. 169: 265 (1978); S. Seifter and E. Harper, Chap. 18, "The Collagenases" in The Enzymes (3rd Ed.) 3: 649–697, Ed. by P. D. Boyer, Academic Press, N.Y.

(1971)]. In the eye, a number of studies using collagenase inhibitors directly applied to corneal ulcerations have been reported. Calcium ethylenediaminetetraacetate and acetylcysteine reduce the frequency of ulceration in the alkali burned rabbit [M. Berman and C. Dohlman, Arch. Ophthalmol. 35: 95 (1975)]. Both cysteine and acetylcysteine have been effective in the treatment of acute and chronic corneal ulceration in the human, although the latter compound was preferred because of its greater stability [S. I. Brown, N. P. Tragakis and D. B. Pease, Am. J. Ophthalmol. 74: 316 (1972); M. Berman, "Trace Components of Plasma: Isolation and Clinical Significance," 7th Annual Red Cross Symposium, p. 225, Alan R. Liss, Inc., N.Y. (1976)].

Naturally occurring collagenase inhibitors include the serum components $\alpha_2$-macroglobulin and $\beta_1$-anticollagenase [D. E. Woolley, R. W. Glanville, D. R. Roberts and J. M. Evanson, Biochem. J. 169: 265 (1978)].

While some compounds may inhibit the destructive effect of collagenase on connective tissue by acting directly on collagenase itself, other compounds may inhibit such destruction by coating, binding or competing with sites on the connective tissue in such a manner as to prevent collagenase from attacking it. The present invention, however, is not to be restricted or limited to any particular mechanism or mode of action. Suffice it to say, that the compounds of this invention have utility as inhibitors of connective tissue destruction albeit in whatever manner or mode.

U.S. Pat. No. 2,687,436 discloses substituted 3-(2-naphthyl)-cyclohexanes useful in the treatment of collagen diseases. British Pat. Nos. 856,357 and 1,246,141 disclose 2-aryl-hexahydro-quinolizines and 1-hydroxylpraline derivatives, respectively, useful for treating diseases affecting connective tissue. The closest known structurally related compound to those of the present invention and disclosed as having collagenase inhibiting activity is found in Thromb Res. 10(4): 605–11 (1977), wherein the trypanocidal agent trypan blue is reported as inhibiting the activity of collagenase, or a proteinase contaminant in the collagenase preparation. It is interesting, however, that in this same article, the ureide Suramin is reported as not inhibiting the action of collagenase.

U.S. Pat. Nos. 4,046,805; 4,127,602; and 4,129,590 disclose the compounds of the present invention as complement inhibitors, but these compounds have no known disclosure as inhibitors of connective tissue destruction or as collagenase inhibitors. These known compounds pertinent to the present invention are collectively represented by the following generic formula:

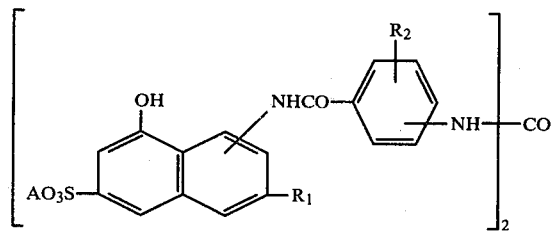

wherein A is selected from the group consisting of hydrogen and a nontoxic pharmaceutically acceptable cation salt; $R_1$ is selected from the group consisting of hydrogen and $-SO_3A$; and $R_2$ is selected from the group consisting of hydrogen, ortho $-SO_3A$ and ortho- or meta-methyl.

Certain other ureides are disclosed in J. Chem. Soc. 3069 (1927), and U.S. Pat. Nos. 1,218,654 and 1,308,071 but these publications do not disclose a utility for inhibition of connective tissue destruction or collagenase inhibition. The generic disclosure of U.S. Pat. No. 1,308,071 encompasses a vast number of ureides but does not render obvious the invention claimed herein.

SUMMARY OF THE INVENTION

It has now been discovered that certain ureides of substituted naphthalenesulfonic acids and salts thereof inhibit connective tissue destruction.

This invention is concerned with a novel method of inhibiting connective tissue destruction in a warm-blooded animal which comprises administering to said animal an effective inhibiting amount of a known compound of the formula:

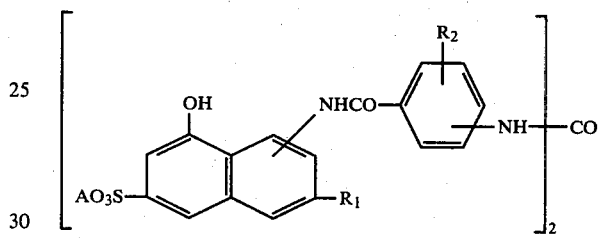

wherein A is selected from the group consisting of hydrogen and a pharmaceutically acceptable cation salt; $R_1$ is selected from the group consisting of hydrogen and $-SO_3A$; and $R_2$ is selected from the group consisting of hydrogen, ortho-$SO_3A$ and ortho- or meta-methyl.

This invention is also concerned with a new method of inhibiting the degradation sequelae of collagenase activity in a body fluid which comprises subjecting body fluid collagenase to the action of an effective collagenase inhibiting amount of a compound encompassed within the above formula. This invention is further concerned with a method of inhibiting the action of collagenase in a warm-blooded animal which comprises internally administering to said animal an effective collagenase inhibiting amount of a compound encompassed within the above formula.

DETAILED DESCRIPTION OF THE INVENTION

This invention is concerned with three novel methods of use of compounds represented by the following generic formula:

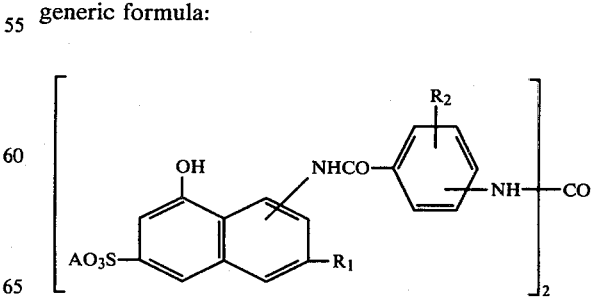

wherein A is selected from the group consisting of hydrogen and a pharmaceutically acceptable cation salt;

$R_1$ is selected from the group consisting of hydrogen and $-SO_3A$; and $R_2$ is selected from the group consisting of hydrogen, ortho-$SO_3A$ and ortho- or meta-methyl.

The first new method of use of this invention is a method of inhibiting connective tissue destruction in a warm-blooded animal which comprises administering to said animal an effective inhibiting amount of a compound of the above formula. The second new method of use of the invention regards a method of inhibiting the degradation sequelae of collagenase activity in a body fluid by subjecting body fluid collagenase to the action of an effective collagenase inhibiting amount of a known compound of the above formula. Body fluid containing collagenase can include blood, plasma, serum, synovial fluid, crevicular fluid, ocular fluid, etc. The third new method of use of this invention deals with a method of inhibiting the action of collagenase in a warm-blooded animal which comprises administering internally to said animal an effective collagenase inhibiting amount of a compound encompassed within the above formula.

Since the compounds of the present invention are useful as inhibitors of connective tissue destruction or as collagenase inhibitors in body fluids, they find utility in the amelioration or prevention of those pathological reactions resulting from the functioning of collagenase, and in the therapeutic treatment of warm-blooded animals having connective tissue disorders such as periodontal diseases and diseases of the teeth, osteoporosis, osteolysis, Paget's disease, hyperparathyroidism of renal failure, rheumatoid arthritis, septic arthritis, osteoarthritis, gout, acute synovitis, scleroderma, psoriasis, epidermolysis bullosa, keloids, blisters, cholesteatoma of the ear, and corneal ulceration. The compounds of the present invention may also be useful in those pathological states where excessive activity of neutral proteases causes tissue damage.

Particularly preferred compounds of this invention which are of major interest as inhibitors of connective tissue destruction include the following:

4,4'-[Ureylenebis(m-phenylenecarbonylimino)]bis[5-hydroxy-2,7-naphthalenedisulfonic acid]tetrasodium salt 3,3'-[Ureylenebis(m-phenylenecarbonylimino)]bis[5-hydroxy-2,7-naphthalenedisulfonic acid]tetrasodium salt 4,4'-[Ureylenebis(3-methyl-p-phenylenecarbonylimino)]bis[5-hydroxy-2,7-naphthalenedisulfonic acid]tetrasodium salt 4,4'-[Ureylenebis(2-methyl-3,1-phenylenecarbonylimino)]bis[5-hydroxy-2,7-naphthalenedisulfonic acid]tetrasodium salt 4,4'-[Ureylenebis(6-methyl-3,1-phenylenecarbonylimino)]bis[5-hydroxy-2,7-naphthalenedisulfonic acid]tetrasodium salt 5,5'-[Ureylenebis(2-sulfo-4,1-phenylenecarbonylimino)]bis[4-hydroxy-2-naphthalenesulfonic acid]tetrasodium salt The compounds of the present invention may be prepared according to Flowchart A. See U.S. Pat. Nos. 4,046,805; 4,127,602; and 4,129,590.

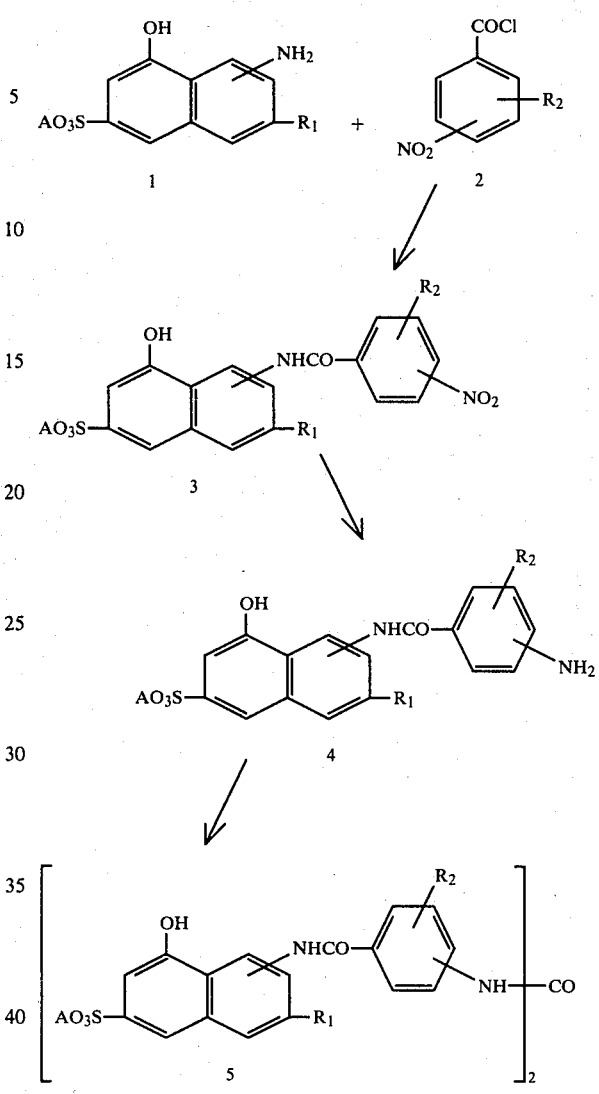

With reference to Flowchart A, a substituted-aminonaphthalenesulfonic acid 1 is dissolved in water, made basic with any suitable base such as, for example, an alkali acetate or alkali metal carbonate, reacted with an alkali acetate such as sodium acetate, filtered and reacted under an inert atmosphere, e.g., nitrogen, with an excess substituted nitrobenzoyl chloride 2, giving a substituted nitrobenzamido-substituted-naphthalenesulfonic acid 3. This nitro derivative 3 is then hydrogenated in the presence of a suitable catalyst, giving the corresponding amine derivative 4. The amine 4 is dissolved in a basic solution of pyridine and water and then phosgenated. The final ureide product 5 is extracted from conventional organic solvents such as ethanol or ether. The resulting compound may be converted to its salt in a known manner.

It is generally preferred that the respective product of each process step, described hereinabove, is separated and/or isolated prior to its use as starting material for subsequent steps. Separation and isolation can be effected by any suitable purification procedure such as, for example, evaporation, crystallization, column chromatography, thin-layer chromatography, distillation, etc. Also, it should be appreciated that when typical reaction conditions (e.g., temperatures, mole ratios, reaction times) have been given, the conditions which are both above and below these specified ranges can also be used, though generally less conveniently.

The term "pharmaceutically acceptable salts" refers to those salts of the parent compound which do not significantly or adversely affect the pharmaceutical properties (e.g., toxicity, effectiveness, etc.) of the parent compound, such as those salts that are conventionally used in the pharmaceutical art. The salts of the present invention which are pharmaceutically acceptable include, for example, the alkali metals (e.g., sodium, potassium, lithium, etc.), alkaline earth metals (e.g., calcium, magnesium, etc.), ammonium, primary amines (e.g., ethylamine), secondary amines (e.g., diethylamine or diethanolamine), tertiary amines (e.g., pyridine, triethylamine or 2-dimethylaminomethyldibenzofuran), aliphatic diamines (e.g., decamethylenediamine) and aromatic diamines.

As used hereinabove and below unless expressly stated to the contrary, all temperatures and temperature ranges refer to the centigrade system and the terms "ambient" or "room temperature" refer to about 20° C. The term "percent" or "(%)" refers to weight percent and the terms "mole" and "moles" refer to gram moles. The term "equivalent" refers to a quantity of reagent equal in moles to the moles of the preceding or succeeding reactant recited in the Preparation or Example in the term of moles of finite weight or volume.

A further understanding of the invention can be obtained from the following non-limiting Preparations and Examples. Although the compounds of this invention are known, having been disclosed in U.S. Pat. Nos. 4,046,805; 4,127,602; or 4,129,590, they are reproduced below for convenience.

EXAMPLE 1

4-(3-Amino-p-toluamido)-5-hydroxy-2,7-naphthalenedisulfonic acid, disodium salt

A mixture of 25.0 g of 4-hydroxy-5-(3-nitro-p-toluamido)-2,7-naphthalenedisulfonic acid, disodium salt, 200 ml of distilled water and 2.5 g of 10% palladium on charcoal is hydrogenated in a Parr shaker for 3½ hours at room temperature during which time 12 pounds of hydrogen is absorbed. The mixture is heated on a steam bath and is filtered through diatomaceous earth to remove the catalyst. The filter is washed with hot water and the filtrate is then evaporated to a low volume in vacuo at 55°–60° C. and diluted with a large amount of absolute ethyl alcohol. The precipitate formed is triturated with a glass rod to break up any lumps and is allowed to stand at room temperature overnight, then is filtered and is washed with absolute ethyl alcohol and ether. The product of the example is oven dried at 120° C. overnight.

EXAMPLE 2

4,4'[Ureylenebis(m-phenylenecarbonylimino)]bis[5-hydroxy-2,7-naphthalenedisulfonic acid]tetrasodium salt A mixture of 11.32 g of 4-hydroxy-5-m-nitrobenzamido-2,7-naphthalenedisulfonic acid, disodium salt, 150 ml of distilled water and 0.5 g of 10% palladium on charcoal is hydrogenated in a Parr shaker for 3 hours at room temperature during which time 13 pounds of hydrogen is absorbed. The mixture is heated on a steam bath and is filtered through diatomaceous earth to remove the catalyst. The filter is washed with hot water and the filtrate is cooled to room temperature, then 1.83 g of concentrated hydrochloric acid is added and the precipitate formed is dissolved by boiling. The aqueous solution is concentrated to about 175 ml, 100 ml of absolute ethyl alcohol is added and the resultant mixture allowed to come to room temperature overnight. The precipitate formed, which is 4-m-amino-benzamido-5-hydroxy-2,7-naphthalenedisulfonic acid, 2-sodium salt, is collected by filtration.

To a stirred solution of 10 g of the above product, prepared in the same manner, and 34.5 g of anhydrous sodium carbonate in 250 ml of water is bubbled in phosgene at ambient temperature. After 2 hours an additional 17 g of sodium carbonate is added and the phosgene addition is continued for another hour. The precipitate formed is collected, mixed with water, neutralized with base, then heated and filtered. The material collected is dissolved in 300 ml of hot water, then concentrated to 200 ml in vacuo. The gelatinous precipitate is collected by slow filtration and then stirred with 95% ethyl alcohol. The resulting product is filtered and washed with diethyl ether to give the desired product.

EXAMPLE 3

4,4'-[Ureylenebis(2-methyl-1,3-phenylenecarbonylimino)]bis[5-hydroxy-2,7-naphthalenedisulfonic acid]

The aqueous phase filtrate set aside at the conclusion of Example 1 is concentrated in vacuo at about 50°–60° C. and filtered. The filtrate is evaporated to dryness and triturated with about 250 ml of boiling methyl alcohol, then filtered. This filtrate is evaporated in vacuo to afford a brown solid which is dissolved in 10 ml of distilled water. The solution is then warmed on a steam bath and diluted with about 30 ml of absolute ethyl alcohol to give a black viscous material. The supernatant is decanted and absolute alcohol is added to the residue with scratching to afford a precipitate which is collected by filtration. This material is dissolved in 10 ml of distilled water, boiled, then treated with activated charcoal and filtered through diatomaceous earth. The filtrate is diluted two-fold with absolute ethyl alcohol and the upper phase is decanted from a dark oil. The decanted liquid is acidified with concentrated hydrochloric acid and evaporated to dryness in vacuo. The residue is dissolved in 5 ml of dimethylformamide, filtered to remove sodium chloride, then washed with 5 ml of dimethylformamide. The combined filtrate and washing is diluted with a few ml of methyl alcohol and a large volume of diethyl ether to yield a dark brown oil. The supernatant is decanted and acetone added to the residue with scratching until a solid forms which is collected by filtration and washed with acetone. The desired product is then oven dried at 105° C. overnight.

EXAMPLE 4

3,3'-[Ureylenebis(m-phenylenecarbonylimino)]bis[5-hydroxy-2,7-naphthalenedisulfonic acid]tetrasodium salt A 41.0 g portion of recrystallized 3-amino-5-hydroxy-2,7-naphthalenedisulfonic acid and 16.5 g of sodium acetate trihydrate are dissolved in 250 ml of distilled water, then 44.55 g of m-nitrobenzoyl chloride is added all at once along with 120 ml of 1 N sodium hydroxide and a small amount of diethyl ether. The resulting mixture is shaken for 5 minutes, another 120 ml of 1 N sodium hydroxide and a small amount of diethyl ether. The resulting mixture is shaken for 5 minutes, another 120 ml of 1 N sodium hydroxide is added and the mixture is shaken for ½ hour. The latter addition and shaking is repeated two more times. The resulting mixture is acidified to Congo Red indicator paper with concentrated hydrochloric acid and allowed to stand at 5° C. for 17 hours. The solution is filtered and the filtrate allowed to stand until a precipitate forms. The precipitate is stirred with about 400 ml of diethyl ether and collected to give 5-hydroxy-3-m-nitrobenzamido-2,7-naphthalenedisulfonic acid, disodium salt.

A mixture of 15.5 g of the preceding compound (prepared as described above), 170 ml of distilled water and 1.02 g of 10% palladium on charcoal is hydrogenated in a Parr shaker for 1½ hours at room temperature during which time 8.5 pounds of hydrogen is absorbed. The mixture is heated to dissolve some precipitated product and filtered hot to remove the catalyst. The filtrate is then evaporated to a low volume and the precipitate formed is collected with the aid of 95% ethyl alcohol and washed with diethyl ether to give 3-(m-aminobenzamido)-5-hydroxy-2,7-naphthalenedisulfonic acid, disodium salt. Phosgene is bubbled into a stirred solution of 10 g of the product prepared in the manner described above and 34.5 g of anhydrous sodium carbonate in 250 ml of water at ambient temperature. After one hour and 15 minutes an additional 34.5 g of sodium carbonate is added and the phosgene addition is continued until it is acidic again (5 hours). The solution is then neutralized with base and filtered. The filtrate is concentrated and filtered and the final filtrate is concentrated and filtered. All the residues are combined and dissolved in 250 ml of hot water which is concentrated to 150 ml, cooled and the precipitate formed is collected by filtration. The precipitate is dissolved in hot water and concentrated to a low volume until a precipitate is formed which is collected by filtration with the aid of 95% ethyl alcohol to give the desired product.

EXAMPLE 5

5-(4-Amino-2-sulfobenzamido)-4-hydroxy-2-naphthalenesulfonic acid disodium salt

An 11.1 g portion of 1-amino-8-naphthol-6-sulfonic acid is dissolved in 100 ml of water and neutralized to pH 7, then 8.56 g of sodium acetate trihydrate is added with stirring. With continued stirring, 10.88 g of 4-nitro-2-sulfobenzoic acid anhydride is added all at once. The resulting mixture is stirred for 30 minutes and the residue is filtered and set aside. The filtrate is acidified with 3.5 ml of concentrated hydrochloric acid and concentrated. The residue is slurried in water and filtered. The precipitate is washed with ethyl alcohol and ether and dried to yield 4.0 g of a solid. The residue set aside previously is recycled as above using one-half the amounts of sodium acetate and the mixed anhydride. To the resulting mixture is added a quantity of base sufficient to cause almost complete solution and stirring is continued for 20 minutes. The mixture is filtered and the filtrate is acidified and concentrated to about ½ volume with separation of a solid. This material is collected by filtration, washed with ethyl alcohol and ether, and dried to give 2.9 g of an orange solid, giving a total yield of 6.9 g of 4-hydroxy-5-(4-nitro-2-sulfobenzamido)-2,7-naphthalenedisulfonic acid disodium salt.

A 5.12 g portion of the above product is stirred in 250 ml of water, then is filtered. To the filrate is added 1.0 g of palladium catalyst on charcoal, then the mixture is hydrogenated until no additional hydrogen is absorbed. The mixture is filtered through diatomaceous earth and concentrated. Two crystallizations with ethyl alcohol from aqueous solution yields a total of 4.4 g of the desired product which is washed with ethyl alcohol and ether and dried.

EXAMPLE 6

5,5'-[Ureylenebis(2-sulfo-4,1-phenylenecarbonylimino)]bis[4-hydroxy-2-naphthalenesulfonic acid]tetrasodium salt Phosgene gas is passed into a solution of 4.1 g of the product of Example 5, and 1.81 g of sodium carbonate in 35 ml of water until it is acidic to Congo Red indicator. The cooled solution is adjusted to pH 8 by the addition, with stirring, of more sodium carbonate, then is adjusted to pH 6.5 with acetic acid. The resulting mixture is filtered and concentrated. The residue is dissolved in 40 ml of hot water, then is cooled with formation of a precipitate. The product is collected by filtration, washed with some water, then with ethyl alcohol and ether and dried by conventional means to yield 1.6 g of the desired product.

EXAMPLE 7

4,4'-[Ureylenebis(3-methyl-p-phenylenecarbonylimino)]bis[5-hydroxy-2,7-naphthalenedisulfonic acid]tetrasodium salt A reaction mixture comprising 10.0 g of 4-(4-amino-m-toluamido)-5-hydroxy-2,7-naphthalenedisulfonic acid disodium salt and 21.4 g of anhydrous sodium carbonate in 250 ml of water is phosgenated for 45 minutes until acid to Congo Red. A 21.4 g portion of anhydrous sodium carbonate is added and phosgenation is continued for 30 minutes. The reaction mixture is concentrated at 55° C. to about 100 ml and allowed to stand overnight. The solid is collected and washed with absolute alcohol and ether. This solid is boiled in 250 ml of methanol, filtered and washed with methanol. This solid is dissolved in 100 ml of hot water, diluted with 100 ml of absolute ethanol, filtered after cooling to room temperature and washed with 90% ethanol, absolute ethanol and ether. This solid is dissolved in 200 ml of boiling water, filtered and the filtrate diluted with 200 ml of absolute ethanol. The solid is collected, washed with absolute ethanol and ether giving 3.64 g of the desired final product.

EXAMPLE 8

4,4'-[Ureylenebis(6-methyl-3,1-phenylenecarbonylimino)]bis[5-hydroxy-2,7-naphthalenedisulfonic acid]tetrasodium salt A mixture of 74.5 g of 2-methyl-5-nitrobenzoic acid and 160 ml of thionyl chloride is refluxed for 4½ hours (complete solution after 1½ hours). The mixture is evaporated in vacuo to an oil, then is reevaporated several times with toluene, finally about 300 ml of hexane is added resulting in formation of needles after standing at room temperature overnight. The material is collected by filtration and is washed with hexane to give 5-nitro-o-toluoyl chloride.

A 26.9 g portion of recrystallized 4-amino-5-hydroxy-2,7-naphthalenedisulfonic acid, monosodium salt and 10.0 g of sodium acetate trihydrate is suspended in 125 ml of distilled water, then 75 ml of 1 N sodium hydroxide is added and 16.5 g of 5-nitro-o-toluoyl chloride is added all at once washing in with a small amount of diethyl ether. The resulting mixture is shaken for 5 minutes. The addition of two more 75 ml portions of 1 N sodium hydroxide is required with shaking for 45 minutes after the last addition. The mixture is then acidified with 13 ml of concentrated hydrochloric acid and is extracted with six 150 ml portions of diethyl ether which is removed by vacuum siphoning after each extraction. The aqueous phase is then neutralized with base and 6 drops of n-decyl alcohol is added to prevent frothing. The solution is then concentrated to a low volume in vacuo and diluted with a saturated saline solution to produce a precipitate. The precipitated product is filtered very slowly and washed with absolute ethanol followed by ether. The lumpy material is oven dried at 120° C. for several hours then is dissolved in about 600 ml of boiling water and diluted with 150 ml of absolute ethanol. The precipitate containing 4-hydroxy-5-(5-nitro-o-toluamido)-2,7-naphthalenedisulfonic acid, disodium salt, formed after standing at room temperature overnight, is collected by filtration and washed with absolute ethanol followed by ether, then oven dried overnight at 120° C.

A mixture of 25.0 g of 4-hydroxy-5-(5-nitro-o-toluamido)-2,7-naphthalenedisulfonic acid, disodium salt, 200 ml of distilled water and 2.5 g of 10% palladium on charcoal is hydrogenated in a Parr shaker for 5 hours at room temperature during which time 12 pounds of hydrogen is absorbed. The mixture is heated on a steam bath and filtered through diatomaceous earth to remove the catalyst. The filter is washed with hot water and the filtrate is then evaporated to about 100 ml in vacuo at 55°-60° C. with formation of crystals after standing at room temperature overnight. The product, 4-(5-amino-o-toluamido)-5-hydroxy-2,7-naphthalenedisulfonic acid, disodium salt, is collected by filtration and washed with absolute ethanol followed by ether, then oven dried at 120° C.

A solution of 12.0 g of 4-(5-amino-o-toluamido)-5-hydroxy-2,7-naphthalenedisulfonic acid, disodium salt and 12.1 ml of pyridine in 250 ml of water is phosgenated in a water bath until acidic to Congo Red. A 6 ml portion of pyridine is added and the phosgenation is repeated. The mixture is neutralized to pH 5 with pyridine, concentrated to 100 ml and then added dropwise to 1400 ml of ethanol. The solid is filtered, washed with ethanol and ether and dried. This solid is dissolved in 100 ml of water, the pH is adjusted to 8-9 with 5 N sodium hydroxide and then back neutralized to pH 7 with acetic acid. The solution is slowly added to one liter of ethanol. The solid is collected, washed with ethanol, acetone and ether and dried giving 6.0 g of the desired product.

EXAMPLE 9

Preparation of Compressed Tablet

| Ingredient | mg/Tablet |
| --- | --- |
| Active Compound | 0.5-500 |
| Dibasic Calcium Phosphate NF | qs |
| Starch USP | 40 |
| Modified Starch | 10 |
| Magnesium Stearate USP | 1-5 |

EXAMPLE 10

Preparation of Compressed Tablet—Sustained Action

| Ingredient | mg/Tablet |
| --- | --- |
| Active Compound as Aluminum Lake*, Micronized | 0.5-500 (as acid equivalent) |
| Dibasic Calcium Phosphate NF | qs |
| Alginic Acid | 20 |
| Starch USP | 35 |
| Magnesium Stearate USP | 1-10 |

*Collagenase inhibitor plus aluminum sulfate yields aluminum collagenase inhibitor. Collagenase inhibitor content in aluminum lake ranges from 5-30%

EXAMPLE 11

Preparation of Hard Shell Capsule

| Ingredient | mg/Capsule |
| --- | --- |
| Active Compound | 0.5-500 |
| Lactose, Spray Dried | qs |
| Magnesium Stearate | 1-10 |

EXAMPLE 12

Preparation of Oral Liquid (Syrup)

| Ingredient | % W/V |
| --- | --- |
| Active Compound | 0.05-5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 13

Preparation of Oral Liquid (Elixir)

| Ingredient | % W/V |
| --- | --- |
| Active Compound | 0.05-5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 14

Preparation of Oral Suspension (Syrup)

| Ingredient | % W/V |
| --- | --- |
| Active Compound as Aluminum Lake, Micronized | 0.05-5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 15

Preparation of Injectable Solution

| Ingredient | % W/V |
| --- | --- |
| Active Compound | 0.05–5 |
| Benzyl Alcohol NF | 0.9 |
| Water for Injection | 100.0 |

EXAMPLE 16

Preparation of Injectable Oil

| Ingredient | % W/V |
| --- | --- |
| Active Compound | 0.05–5 |
| Benzyl Alcohol | 1.5 |
| Sesame Oil qs ad | 100.0 |

EXAMPLE 17

Preparation of Intra-Articular Product

| Ingredient | Amount |
| --- | --- |
| Active Compound | 2–20 mg |
| NaCl (physiological saline) | 0.9% |
| Benzyl Alcohol | 0.9% |
| Sodium Carboxymethylcellulose | 1.5% |
| pH adjusted to 5.0–7.5 | |
| Water for Injection qs ad | 100% |

EXAMPLE 18

Preparation of Injectable Depo Suspension

| Ingredient | % W/V |
| --- | --- |
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol NF | 0.9 |
| HCl to pH 6–8 | qs |
| Water for Injection qs ad | 100.0 |

EXAMPLE 19

Preparation of Dental Paste

| Ingredient | % W/W |
| --- | --- |
| Active Compound | 0.05–5 |
| Zinc Oxide | 15 |
| Polyethylene Glycol 4000 USP | 50 |
| Distilled Water qs | 100 |

EXAMPLE 20

Preparation of Dental Ointment

| Ingredient | % W/W |
| --- | --- |
| Active Compound | 0.05–5 |
| Petrolatum, White USP qs | 100 |

EXAMPLE 21

Preparation of Dental Cream

| Ingredient | % W/W |
| --- | --- |
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 22

Preparation of Topical Cream

| Ingredient | % W/W |
| --- | --- |
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 23

Preparation of Topical Ointment

| Ingredient | % W/W |
| --- | --- |
| Active Compound | 0.05–5 |
| Cholesterol | 3 |
| Stearyl Alcohol | 3 |
| White Wax | 8 |
| Petrolatum, White USP qs | 100 |

EXAMPLE 24

Preparation of Spray Lotion (Non-aerosol)

| Ingredient | % W/W |
| --- | --- |
| Active Compound | 0.05–5 |
| Isopropyl Myristate | 20 |
| Alcohol (Denatured) qs | 100 |

EXAMPLE 25

Preparation of Buccal Tablet

| Ingredient | mg/Tablet |
| --- | --- |
| Active Ingredient | 3.25 |
| 6 x Sugar | 290.60 |
| Acacia | 14.53 |
| Soluble Starch | 14.53 |
| F. D. & C. Yellow No. 6 Dye | 0.49 |
| Magnesium Stearate | 1.60 |
| | 325.00 |

The final tablet will weigh about 325 mg and may be compressed into buccal tablets in flat faced or any other tooling shape convenient for buccal administration.

EXAMPLE 26

Preparation of Lozenge

| Ingredient | g/Lozenge |
|---|---|
| Active Ingredient | 0.0140 |
| Kompact ® Sugar (Sucrest Co.) | 0.7138 |
| 6 x Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅝" flat based lozenge tooling. Other shapes may also be utilized.

EXAMPLE 27

Preparation of Gelled Vehicles

| Ingredient | % W/W |
|---|---|
| Active Compound | 9-11 |
| Sodium Chloride | 0.9-1.2 |
| Buffer and Flavor qs | — |
| Purified Water qs ad | 100 |
| Active Compound | 0.005-9 |
| Sodium Alginate | 0.5-2 |
| Buffer and Flavor qs | — |
| Purified Water qs ad | 100 |
| Active Compound | 0.005-9 |
| Hydroxypropyl Cellulose | 0.5-2 |
| Buffer and Flavor qs | — |
| Purified Water qs ad | 100 |
| Active Compound | 0.005-9 |
| Guar Gum | 0.5-2 |
| Buffer and Flavor qs | — |
| Purified Water qs ad | 100 |

EXAMPLE 28

Preparation of Oral Mouth Rinse

| Ingredient | % W/V |
|---|---|
| Active Compound | 0.05-20 |
| Alcohol USP | 0-20 |
| Sorbitol | 1-30 |
| Buffer and Flavor qs | — |
| Polysorbate 80 | 0.1-3 |
| Cetyl Pyridinium Chloride | 0.025-0.20 |
| Purified Water qs ad | 100 |

EXAMPLE 29

Preparation of Tooth Paste

| Ingredient | % W/W |
|---|---|
| Active Compound | 0.05-15 |
| Glycerin | 5-15 |
| Sorbitol | 5-15 |
| Sodium Carboxymethylcellulose | 0.5-2 |
| Magnesium Aluminum Silicate | 0.1-1 |
| Carrageenin | 0.25-2 |
| Preservative qs | — |
| Sodium Lauryl Sulfate | 0.1-3 |
| Calcium Carbonate | 25-45 |
| Flavor qs | — |
| Purified Water qs ad | 100 |

EXAMPLE 30

Preparation of Dental Paste

| Ingredient | % W/W |
|---|---|
| Active Compound | 0.05-20 |
| Carboxymethylcellulose | 5-20 |
| Pectin | 5-20 |
| Plastibase ® | 20-70 |
| Gelatin | 5-20 |

EXAMPLE 31

Preparation of Dental Ointment

| Ingredient | % W/W |
|---|---|
| Active Compound | 0.05-20 |
| Polyethylene Glycol 4000 | 50-80 |
| Polyethylene Glycol 400 | 10-40 |

EXAMPLE 32

Preparation of Dental Powder for Brushing or for Use in Water Spray (e.g., Water Pik ®)

| Ingredient | % W/W |
|---|---|
| Active Compound | 0.05-10 |
| Flavor qs | — |
| Wetting Agents qs | — |
| Dextrin qs ad | 100 |

EXAMPLE 33

Preparation of Stick for Application to Gums

| Ingredient | % W/W |
|---|---|
| Active Compound | 0.05-10 |
| Glycerin | 5-10 |
| Propylene Glycol | 40-80 |
| Sodium Stearate | 6-10 |
| Flavor qs | — |
| Water | 0-10 |

EXAMPLE 34

Preparation of Periodontal Packing Paste

| Ingredient | % W/W |
|---|---|
| Paste Part A | |
| Active Compound | 0.05-20 |
| Caprylic Acid | 9.0 |
| Lauric Acid | 27.0 |
| Ethylcellulose (100 cps.) | 2.0 |
| Polypale Resin* | 39.0 |
| Gum Elemi | 4.0 |
| Brominol** | 4.0 |
| Mica (Powdered) | 7.5 |
| Chlorothymol | 1.0 |
| Zinc Acetate | 2.0 |
| Bay Oil (Essential Oil) | 1.0 |
| Ethanol | 1.5 |
| Paste Part B | |
| Magnesium Oxide | 43.0 |
| Zinc Oxide | 21.0 |
| Calcium Hydroxide | 3.5 |
| Copper Oxide | 2.0 |
| Mineral Oil, Heavy | 26.0 |
| Rosin Oil | 3.0 |

| Ingredient | % W/W |
|---|---|
| Chlorothymol | 1.4 |
| Cumarin (Flavor) | 0.1 |

*Partially polymerized rosin (i.e., modified rosin)
**Brominated olive oil

When equal parts of A and B are mixed together at 25° C., a hard mass is formed in about 3 minutes.

EXAMPLE 35

Preparation of Periodontal Packing Paste

| Ingredient | % W/W |
|---|---|
| Part A (Powder) | |
| Active Compound | 0.05–20 |
| Canada Balsam, Neutral | 8.5 |
| Rosin NF | 8.5 |
| Calcium Hydroxide | 34.4 |
| Zinc Oxide USP | 46.6 |
| Part B (Liquid Hardener) | |
| Eugenol | 85.0 |
| Turpentine Oil, Rectified | 15.0 |

A mixture of three drops of Part B added to 130 mg of Part A produces a hard mass in about 2–3 minutes at 30° C.

The compounds of this invention may be administered internally, e.g., orally, intra-articularly or parenterally, to a warm-blooded animal to inhibit connective tissue destruction or collagenase, such inhibition being useful in the amelioration or prevention of those reactions causing connective tissue damage. A range of doses may be employed depending on the mode of administration, the condition being treated and the particular compound being used. For example, for intravenous or subcutaneous use from about 5 to about 50 mg/kg/day, of every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 1.5 mg/kg to about 100 mg/kg of body weight of animal per day. The usual daily dosage for a 70 kg subject may vary from about 100 mg to about 3.5 g. Unit doses can contain from about 0.5 mg to about 500 mg.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate nontoxic dye, so as to provide a pleasing appearance.

The liquid forms in which the novel compositions of the present invention may be incorporated for administration include suitable flavored emulsions with edible oils, such as cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The compounds of the present invention may also be administered topically in the form of ointments, creams, lotions and the like, suitable for the treatment of connective tissue dependent dermatological disorders.

Moreover, the compounds of the present invention may be administered in the form of dental pastes, ointments, buccal tablets and other compositions suitable for application periodontally for the treatment of periodontitis and related diseases of the oral cavity.

The term "dosage unit form" as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention is indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The inhibiting activity of representative compounds of the invention on the destruction of connective tissue has been demonstrated by the following identified test: Collagenase Assay, Test Code 006—This test measures the ability of human skin fibroblast collagenase to degrade radiolabeled native collagen fibrils. An active inhibitor inhibits the degradation of the collagen fibril.

Collagenase Assay—Test Code 006

Collagenase assays were performed by a modification of the method of Harper, et. al., Biochem. 10: 3035 (1971). In a typical assay (total volume of 0.45 ml), 100 µl of the activated enzyme was added to the 14 C- labeled collagen fibrils (250 μl) followed by 100 μl of 50 mM cacodylate, pH 7.4, containing 5 mM calcium chloride. After incubation at 37° C. for 16 hours, the tubes were centrifuged in a Beckman microfuge for five minutes at full speed. An aliquot (200 μl) of the supernatant, representing collagenase digestion products of the fibril, was assayed for radioactivity. The effect of the test compound on collagen degradation by collagenase was examined as follows:

Varying concentrations of the test compound (in distilled water or dimethylacetamide) were added to the assay tubes containing active collagenase (total volume 450 μl) and after 16 hours the amount of radioactivity in the supernatant was determined. Appropriate blanks and trypsin controls were run in parallel.

Table I shows that representative compounds of the invention possess collagenase inhibitory activity. The activities are expressed as % inhibition (lowering) of collagenase activity, i.e., based on the 0% value for the enzyme control.

TABLE I

Biological Activities

| Compound | Test Concentration μg/ml | % Inhibition of Collagenase |
|---|---|---|
| 4,4'-[Ureylenebis(m-phenylenecarbonylimino)]bis[5-hydroxy-2,7-naphthalenedisulfonic acid]tetrasodium salt | 30 | 41 |
| 4,4'-[Ureylenebis(2-methyl-3,1-phenylenecarbonylimino)]bis[5-hydroxy-2,7-naphthalenedisulfonic acid]tetrasodium salt | 30 30 | 32.2 45 |
| 3,3'-[Ureylenebis(m-phenylenecarbonylimino)]bis[5-hydroxy-2,7-naphthalenedisulfonic acid]tetrasodium salt | 30 | 41 |
| 5,5'-[Ureylenebis(2-sulfo-4,1-phenylenecarbonylimino)]bis[4-hydroxy-2-naphthalenesulfonic acid]tetrasodium salt | 30 | 58 |
| 4,4'-[Ureylenebis(3-methyl-p-phenylenecarbonylimino)]bis[5-hydroxy-2,7-naphthalenedisulfonic acid]tetrasodium salt | 30 30 | 78 78 |
| 4,4'-[Ureylenebis(6-methyl-3,1-phenylenecarbonylimino)]bis[5-hydroxy-2,7-naphthalenedisulfonic acid]tetrasodium salt | 30 60 30 30 | 50 39 36 35 |

We claim:

1. A method of inhibiting connective tissue destruction in a warm-blooded animal suffering from connective tissue destruction disease which comprises administering to said warm-blooded animal an effective connective tissue destruction inhibiting amount of a compound selected from those of the formula:

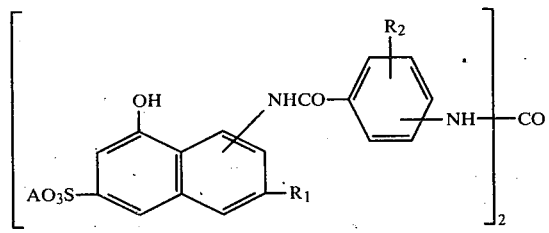

wherein $R_1$ is selected from the group consisting of hydrogen and $-SO_3A$; $R_2$ is selected from the group consisting of hydrogen, ortho-$SO_3A$, ortho-methyl and meta-methyl; and A is selected from the group consisting of hydrogen and a nontoxic pharmaceutically acceptable cation salt.

2. A method of inhibiting the degradation sequelae of collagenase activity in a warm-blooded animal suffering from elevated levels of collagenase which comprises administering to said warm-blooded animals an effective collagenase inhibiting amount of a compound selected from those of the formula:

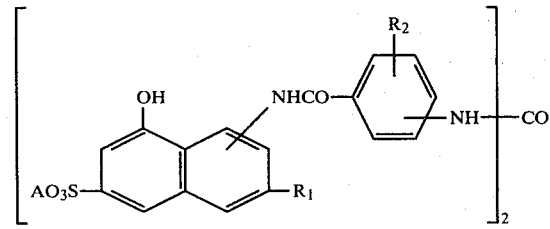

wherein $R_1$ is selected from the group consisting of hydrogen and $-SO_3A$; $R_2$ is selected from the group consisting of hydrogen, ortho-$SO_3A$, ortho-methyl and meta-methyl; and A is selected from the group consisting of hydrogen and a nontoxic pharmaceutically acceptable cation salt.

3. The method according to claim 1 or 2, wherein the compound is 4,4'-[ureylenebis(m-phenylenecarbonylimino)]bis[5-hydroxy-2,7-naphthalenedisulfonic acid]tetrasodium salt.

4. The method according to claim 1 or 2, wherein the compound is 3,3'-[ureylenebis(m-phenylenecarbonylimino)]bis[5-hydroxy-2,7-naphthalenedisulfonic acid]tetrasodium salt.

5. The method according to claim 1 or 2, wherein the compound is 4,4'-[ureylenebis(3-methyl-p-phenylenecarbonylimino)]bis[5-hydroxy-2,7-naphthalenedisulfonic acid]tetrasodium salt.

6. The method according to claim 1 or 2, wherein the compound is 4,4'-[ureylenebis(2-methyl-3,1-phenylenecarbonylimino)]bis[5-hydroxy-2,7-naphthalenedisulfonic acid]tetrasodium salt.

7. The method according to claim 1 or 2, wherein the compound is 4,4'-[ureylenebis(6-methyl-3,1-phenylenecarbonylimino)]bis[5-hydroxy-2,7-naphthalenedisulfonic acid]tetrasodium salt.

8. The method according to claim 1 or 2, wherein the compound is 5,5=-[ureylenebis(2-sulfo-4,1-phenylenecarbonylimino)]bis[4-hydroxy-2-naphthalenesulfonic acid]tetrasodium salt.

9. The method according to claim 1 or 2, wherein the compound is administered internally.

10. The method according to claim 1 or 2, wherein the compound is administered topically.

11. The method according to claim 1 or 2, wherein the compound is administered periodontally in the oral cavity.

12. The method according to claim 1 or 2, wherein the compound is administered intra-articularly.

13. The method according to claim 1 or 2, wherein the compound is administered parenterally.

14. The method according to claim 1, wherein said warm-blooded animal is suffering from periodontal disease.

15. The method according to claim 1, wherein said warm-blooded animal is suffering from diseases of the teeth.

* * * * *